United States Patent [19]

Dequin et al.

[11] Patent Number: 5,712,152
[45] Date of Patent: Jan. 27, 1998

[54] YEAST STRAINS EXPRESSING THE LACTIC LACTICODESHYDROGENASE GENE AND VECTORS USEFUL IN PRODUCING SAID STRAINS

[75] Inventors: Sylvie Dequin, Montpellier; Pierre Barre, Saint-Gely-Du-Fesc, both of France

[73] Assignee: Institut National de la Recherche Agronomique - I.N.R.A., Paris Cedex, France

[21] Appl. No.: 338,509

[22] PCT Filed: Jun. 22, 1993

[86] PCT No.: PCT/FR93/00618

§ 371 Date: Nov. 25, 1994

§ 102(e) Date: Nov. 25, 1994

[87] PCT Pub. No.: WO94/00554

PCT Pub. Date: Jan. 6, 1994

[30] Foreign Application Priority Data

Jun. 23, 1992 [FR] France .................................. 92 07632

[51] Int. Cl.$^6$ .............................. C12N 1/19; C12N 15/31; C12N 15/81

[52] U.S. Cl. .......................... 435/254.21; 435/320.1; 536/23.2; 536/24.1

[58] Field of Search ............................ 435/320.1, 254.2, 435/254.21; 536/23.2, 23.7, 24.1

*Primary Examiner*—James Ketter
*Attorney, Agent, or Firm*—Oblon, Spivak, McClelland, Maier & Neustadt, P.C.

[57] ABSTRACT

Yeast strains containing at least one copy of gene encoding a lactic bacteria lacticodeshydrogenase, under the control of sequences regulating the expression of said gene in the yeast. The invention also encompasses expression vectors for use in producing said yeast strains.

6 Claims, 6 Drawing Sheets

YEAST STRAINS EXPRESSING THE LACTIC LACTICODESHYDROGENASE GENE AND VECTORS USEFUL IN PRODUCING SAID STRAINS

The invention relates to the construction of yeasts expressing an alcoholic/lactic mixed fermentation.

Both of these major types of fermentation of sugars are traditionally employed in the agricultural foodstuffs industry: alcoholic fermentation, for which yeasts of the genus Saccharomyces are responsible, leads chiefly to the formation of ethanol and $CO_2$; and lactic fermentation (lactic bacteria) leads to the formation of lactic acid.

Alcoholic fermentation and lactic fermentation possess metabolic pathways which are almost coincident as far as pyruvate. At this stage, this intermediate is treated differently by two final electron acceptor systems. In alcoholic fermentation, pyruvate is decarboxylated to acetaldehyde, the latter compound being reduced to ethanol by means of an alcohol dehydrogenase; in the lactic fermentation, pyruvate is reduced directly to lactate by means of a lactic dehydrogenase (LDH).

The microorganisms used in agricultural food-stuffs possess one or other of these two metabolic pathways, and accomplish one or other of these two fermentations exclusively.

The inventors undertook to construct a yeast strain capable of accomplishing both alcoholic fermentation and lactic fermentation, resulting in a fermentation having an outcome intermediate between these two types.

The principle of the construction carried out by the inventors consisted in cloning the gene for a lactic dehydrogenase of a GRAS lactic bacterium (*Lactobacillus casei*), and in achieving expression of this gene in Saccharomyces so as to establish therein, at the end of the carbon flux, an electron acceptor system which has to compete with the wild-type system.

Such a construction had never been proposed in the prior art, since it was generally accepted that three major groups of obstacles could stand in the way of its functioning:

- a zero or insufficient expression of the bacterial gene in Saccharomyces;
- a non-competitive functioning of the acceptor system introduced;
- an incompatibility between the functioning of the system and the viability and fermentative activity of Saccharomyces, resulting, for example, from a problem of membrane translocation of lactate.

Now, surprisingly, the inventors have managed to obtain a viable and functional system which leads to the diversion of a large part of the carbon flux towards lactate.

The subject of the present invention is yeast strains, which contain at least one copy of a gene coding for a lactic bacterium LDH, under the control of sequences regulating the expression of said gene in yeast.

Figure 1:
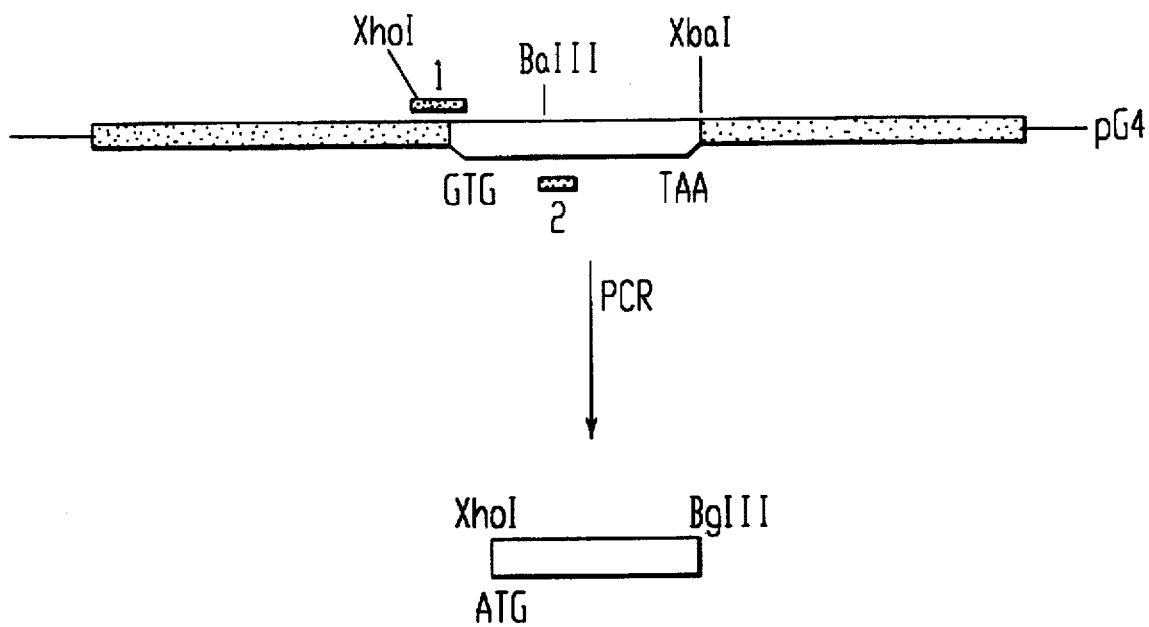
FIG. 1 summarizes the mutagenesis strategy, showing the 3.5 kb insert contained in plasmid pG4 together with the coding region of LDH gene. The PCR primers are also shown (SEQ ID NOS: 5-8).

"Sequences regulating the expression of a gene" are understood to mean sequences of the promoter and terminator type which are active in yeast. The promoters and terminators of different genes may be used, combined in different combinations. The promoters and terminators, known per se, of the alcohol dehydrogenase I (ADHI), phosphoglycerate kinase (PGK) and glyceraldehyde-3-phosphate dehydrogenase (GAPDE) genes may be mentioned by way of a non-limiting example.

The invention also comprises the expression cassette obtained by combining said regulatory sequences and the LDH gene; this cassette may be carried by a plasmid, or integrated in the chromosomal DNA of the host yeast.

According to a preferred embodiment of the present invention, said yeasts belong to the genus Saccharomyces.

According to another preferred embodiment of the present invention, the gene expressed is that for *Lactobacillus casei* LDH.

For the integrated gene to be expressed in yeast, the GTG initiation codon is previously modified to ATG.

The invention also encompasses expression vectors comprising an expression cassette as defined above and which can be used for obtaining the transformed yeast strains according to the invention.

These vectors may be selected on the basis of the nature and strength of the regulatory elements which make up the expression cassette. It is possible to choose the promoters and terminators described above, or any other sequence enabling the expression of a gene in yeast to be controlled.

Another criterion of the choice of vectors lies in the copy number of the latter, which is conditioned by the choice of the origin of replication.

It is possible to choose to integrate the LDH gene, equipped with its control sequences, in the genome of the yeast, in which case an integrative vector (YIp) not possessing an origin of replication in yeast may, for example, be chosen; it is also possible to integrate this gene using other techniques, for example cotransformation.

While it is preferable for the LDn gene to be carried by a plasmid, a choice may be made from among the following vectors:

- High copy number replicative vector (YEp), possessing a portion of the endogenous 2 μ plasmid as origin of replication in yeast;
- High copy number replicative vector (YRp), possessing a chromosomal ARS sequence as origin of replication;
- Linear, high copy number replicative vector (YLp), possessing telomeric sequences as origin of replication;
- Low copy number replicative vector (YCp), possessing a chromosomal ARS sequence and a centromeric sequence.

Preferably, the vectors according to the invention also contain markers which are selectable in yeast, such as markers for auxotrophy: URA3, LEU2, HIS3, TRP1, ADE, and the like, and/or markers for resistance to antibiotics (G418, hygromycin B, chloramphenicol, phleomycin), to herbicides (sulfometuronmethyl), to copper, and the like.

Advantageously, the vectors according to the invention are shuttle vectors, also possessing a bacterial origin of replication and a marker which is selectable in a bacterium (for example an antibiotic-resistance gene).

The plasmids according to the invention carrying the gene coding for the LDH of a lactic bacterium may be introduced into all yeast strains, by different transformation techniques.

Among the commonest transformation techniques, the protoplast technique, the technique of rendering cells permeable to lithium salts and electroporation may be mentioned.

It is possible to modulate the level of expression of the gene coding for LDH, and consequently the ethanol/lactate ratio, by varying, in particular, the number of copies of the LDH gene introduced into the yeast, and/or the strength of the regulatory elements combined therewith.

The construction of different strains according to the invention, expressing LDH to various degrees, may be carried out according to the desired use, which determines the desired ethanol/lactate ratio.

In all cases, the method for this construction comprises the following steps:

construction of an expression cassette comprising the LDH gene and regulatory elements of variable strength, according to the desired ethanol/lactate ratio;

introduction of this cassette, either in single copies or in multiple copies (according to the desired ethanol/lactate ratio), into yeast.

The yeast strains according to the invention find many applications in agricultural foodstuffs. They can be used wherever an alcoholic fermentation has to be accompanied by a biological acidification (for example production of cider from insufficiently acid apples, production of so-called acid bread doughs, kefir type milk products, etc.), or by a lowering of its ethanol output.

This is especially advantageous in the field of enology:

to make up for the lack of acidity of an increasingly large number of wines, in particular in hot regions;

to be able to benefit from the advantages of malolactic fermentation (biological stabilization of the product), even when it leads to an excessively extensive deacidification, by compensating by an acidification;

to produce wines or drinks having a reduced ethanol content.

In addition, taking the deviation from alcoholic fermentation to its extreme, transformed Saccharomyces yeasts according to the invention would make it possible to replace bacteria for carrying out lactic fermentation. These yeasts would possess the following advantages: insensitivity to phages, growth in a neutrient-poor medium, growth in an acid medium, growth at a lower temperature. They might also be employed for the industrial production of lactic acid.

A better understanding of the present invention will be gained from the additional description which follows, which relates to examples of construction of transformed yeast strains according to the invention, as well as to a demonstration of their fermentative activity.

It is, however, self-evident that these examples are given only by way of illustration of the subject of the invention, and in no way constitute a limitation thereof.

EXAMPLE 1

Cloning of the L. casei DNA

A. Construction of an L. casei DNA library in E. coli a) Extraction of L. casei DNA

*Lactobacillus casei* strain ATCC 393 was used. It was cultured on MRS medium, the composition of which is as follows: polypeptone 10 g/l, yeast extract 5 g/l, meat extract 10 g/l, glucose 2 g/l, dipotassium phosphate 2 g/l, sodium acetate 5 g/l, ammonium citrate 2 g/l, magnesium sulfate 0.2 g/l, manganese sulfate 0.05 g/l, Tween 80 1 ml/l.

15 ml of MRS medium are inoculated with *L. casei* and incubated at 37° C. overnight. 500 ml of the same medium are inoculated with the 15 ml of preculture thereby obtained, and incubated at 37° C. with gentle agitation to an OD (550 mm) of 3.9.

The DNA is extracted according to LERCH et al. [Yeast, 7:253–263, (1989)] and purified on a cesium chloride gradient in the presence of ethidium bromide [MANIATIS et al., Molecular cloning: A Laboratory Manual, Cold Spring Harbor Laboratory (1989)].

The ethidium bromide is extracted with isobutanol (twice) and with isoamyl alcohol (twice). After dilution with 2 volumes of water, the DNA is precipitated with 6 volumes of ethanol.

The precipitate is recovered using a rod and dissolved in 2 ml of TE (10 mM Tris, 1 mM EDTA, pH 7.5).

The concentration of the DNA in solution is determined by measuring the OD at 260 nm.

b) Digestion of L. casei DNA

60 µg of *L. casei* DNA are partially digested with 8 units of Sau3A enzyme for 40 min at 37° C.

The mixture is extracted with phenol, phenol/chloroform and chloroform, and precipitated with alcohol.

After centrifugation, the DNA is taken up in 300 µl of TE, and the fragments are separated on a sucrose gradient for 15 hours at 25000 rpm.

0.5-ml fractions are harvested and analyzed on 0.8% agarose gel. The fraction containing 2- to 4-kb fragments is dialyzed against TE for 4 hours.

c) Ligation of the digested DNA to the vector pUC18

The digested DNA is then ligated to the dephosphorylated vector pUC18Bam HI (Appligene), for production of the library, under the following conditions:

|  |  |
| --- | --- |
| pUC18BdP | 5 µl (250 ng) |
| Digested DNA | 10 µl (1 µg) |
| APPLIGENE Tp ligation 5× | 10 µl |
| APPLIGENE ligase | 5 µl |
| Water | 20 µl |

The mixture is incubated for 18 h at 14° C.

d) Transformation of E. coli

*E. coli* strain DH5α (GIBCO BRL), of genotype: F$^{31}$; endA1; hsdR17 (K$^{31}$, mK$^-$); supE44; Thi-1; λ-; recA1; gyrA96; relA1, was used.

The protocols used for the preparation of competent bacteria and those for the transformation are described by HANAHAN [In DNA cloning, vol. 1 D M Glover (ed) IRL Press, 109–135 (1985)].

The ligation mixture was used to transform competent DH5α bacteria. The colonies obtained were selected on LB dishes (bactotryptone 10 g/l, yeast extract 5 g/l, NaCl 10 g/l)+ampicillin (50 µg/ml). 92% of the clones had an insert of the expected size (2–4 kb).

B. Amplification of a fragment of the LDH gene by PCR

On the basis of the protein sequence of *Lactobacillus casei* L-LDH published by HENSEL et al. [Eur. J. Biochem 134:503–511, (1983)], two mixtures of oligonucleotides were synthesized. The primer 4122 is derived from amino acids 5 to 10: Asp-Lys-Asp-His-Gln-Lys (SEQ ID NO. 1), and the primer 5036 is derived from amino acids 262 to 267: Tyr-Met-Asp-Gly-Gln-Tyr (SEQ ID NO. 2) (Kim et al. 1991). 4122: 5'-GA(C,T)-AA(G,A)-GA(C,T)-CA(C,T)-CA(G,A)-A-(A)-3' (SEQ ID NO. 3) 5036: 5'-TA-(C,T)TG-(ACTG)CC-(G,A)TC-CAT-(G,A)TA-3' (SEQ ID NO. 4)

The 2 primers were used to amplify a fragment of the *L. casei* L-LDH gene from the total DNA isolated from this strain; the size of the amplified fragment is 785 base pairs. The amplification was carried out as follows:

| Primer 4122 | 5 µl (100 pmol) |
|---|---|
| Primer 5036 | 7.2 µl (100 pmol) |
| Taq Buffer 10× | 10 µl |
| Taq (BECKMAN) 5u/µl | 0.5 µl |
| dNTP (2 mM) | 10 µl |
| *L. casei* DNA (10 ng/µl) | 10 µl (100 ng) |
| Water | 57 µl |

Taq buffer 10×:100 mM Tris-HCl, pH 8.3, 500 mM KCl, 15 mM MgCl$_2$

Amplification conditions: 1 min at 94° C., 1 min at 55° C., 2 min at 72° C. for 30 cycles, on a TECHNE PHC2 amplifier.

The amplification product is analyzed on 1.5% agarose gel and the corresponding band (785 bp) removed. The DNA is eluted on a MILLIPORE ULTRAFREE column, purified by conventional extractions with phenol, precipitated with alcohol, then centrifuged and taken up in TE buffer.

C. Screening of the library a) Labeling of the 785-bp fragment

The amplified fragment is labeled with $^{32}$p by the multiprime technique using the "Rapid hybridization system—Multiprime" kit (AMERSHAM). The DNA is denatured at 100° C. for 3 min and then cooled abruptly in ice. Labeling is performed under the following conditions:

| 785-base DNA | 12 µl (100 ng) |
|---|---|
| labeling buffer | 10 µl |
| hexanucleotides | 5 µl |
| [$^{32}$P]dCTP (3000 Ci/mmol) | 4 µl |
| Klenow | 2 µl |
| H$_2$O | 17 µl | for 2 hours at 37° C.

The labeled probe is separated from the nucleotides by filtration through a NENSORB column (NEN). The radioactivity of the eluted fractions is determined by counting in a scintillation counter.

b) Preparation of the filters

After the transformation of DH5α bacteria with an aliquot of the ligation mixture constituting the library, 4000 Amp$^r$ clones were obtained on LB+ampicillin dishes, representing approximately 3 times the size of the genome.

The bacterial colonies are transferred onto nylon membranes (HYBOND N, AMERSHAM), and the DNA denatured according to the GRUNSTEIN and HOGNESS technique [Proc. Natl. Acad. Sci. USA 72:3961–3965 (1975)]. The membranes are then incubated for 2 hours at 80° C.

c) Hybridization

Hybridization is carried out using the "Rapid hybridization system—Multiprime" kit according to the protocol described by the supplier (AMERSHAM). The membranes are prehybridized in the hybridization buffer for 15 min at 65° C. The denatured probe is added to the buffer on the basis of 10$^6$ cpm/ml.

Hybridization is carried out at 65° C. overnight.
After hybridization, the membranes are washed:
2 times 10 min at 65° C. with 2×SSPE, 0.1% SDS
1 times 15 min at 65° C. with 1×SSPE, 0.1% SDS
2 times 15 min at 65° C. with 0.7×SSPE, 0.1% SDS
(20×SSPE: 3.6M NaCl; 0.2M NaH$_2$PO$_4$; 0.02M EDTA)

The membranes are subjected to autoradiography for 12 hours at −80° C. with an X-ray film (FUJI).

At the end of the hybridization, a positive clone referred to as pG4 was obtained. The plasmid was extracted from this clone by miniprep (MANIATIS, 1989, reference cited above) and analyzed by digestion with restriction enzymes. Plasmid pG4 contains a 3.5-kb insert of *L. casei* DNA.

Lactate production in *E. coli* was determined for the clone pG4. After growth of pG4 in 10 ml of LB containing 1% of glucose and ampicillin (50 mg/ml) at 37° C., a production of lactate was demonstrated by enzymatic assay using the L-lactate kit (BOEHRINGER).

This confirms that the *L. casei* L-LDH gene is present in its entirety on the 3.5-kb fragment isolated.

EXAMPLE 2

Modification of the Gene by Mutagenesis

The sequence of the *L. casei* LDH gene has been published recently [KIM et al., Appl. Environ. Microbiol. 56:2413–2417, (1991)].

It was verified that the restriction map deduced from the published sequence was identical to that of a central fragment of the 3.5-kb insert of plasmid pG4.

Since the translation initiation codon of the *L. casei* LDH gene is GTG, a codon not used by *Saccharomyces cerevisiae* as an initiation codon, GTG was replaced with ATG by mutagenesis.

The detailed mutagenesis strategy is summarized in FIG. 1 (SEQ ID NOS. 5–8).

1. Obtaining the mutagenized fragment

The 3.5-kb insert contained in plasmid pG4 is shown in FIG. 1, together with the coding region of the LDH gene (GTG start codon, TAA stop codon).

The replacement of GTG with ATG was performed by PCR amplification of a 5' fragment of the gene from plasmid pG4 and using two primers, the position and sequence of which are shown in FIG. 1 (SEQ ID NOS. 5–8):

the primer 1 (SEQ ID NO. 5) consists of 13 bases complementary to the coding region at the 5' end and of 9 different bases: one being an A so as to replace the GTG with ATG, the other 8 enabling an XhoI site to be created on the 5' side of the initiation codon;

the primer 2 (SEQ ID NO. 8) consists of 22 bases complementary to a region internal to the coding region, comprising the BglII site present in the gene.

These 2 primers permit the amplification of a 335-base fragment.

Amplification was carried out in the following manner:

| Primer 1 | 4 µl (20 pmol) |
|---|---|
| Primer 2 | 4 µl (20 pmol) |
| Taq Buffer 10× | 10 µl |
| Taq 5u/µl | 0.5 µl |
| dNTP (2 mM) | 10 µl |
| pG4a | 10 µl 100 ng |
| Water | 70.5 µl |

Amplification conditions: 30 seconds at 94° C., 30 seconds at 55° C., 1 min at 72°C. for 30 cycles.

The size of the amplification fragment was verified (335 bases) by analysis of an aliquot on 1.5% agarose gel.

1.5 µl of the amplification product were digested with XhoI/BglII, and the digested fragment was subcloned into plasmid pBSLDH₃ as described below (2.b).

2. Reconstruction of the gene

Figure 2:
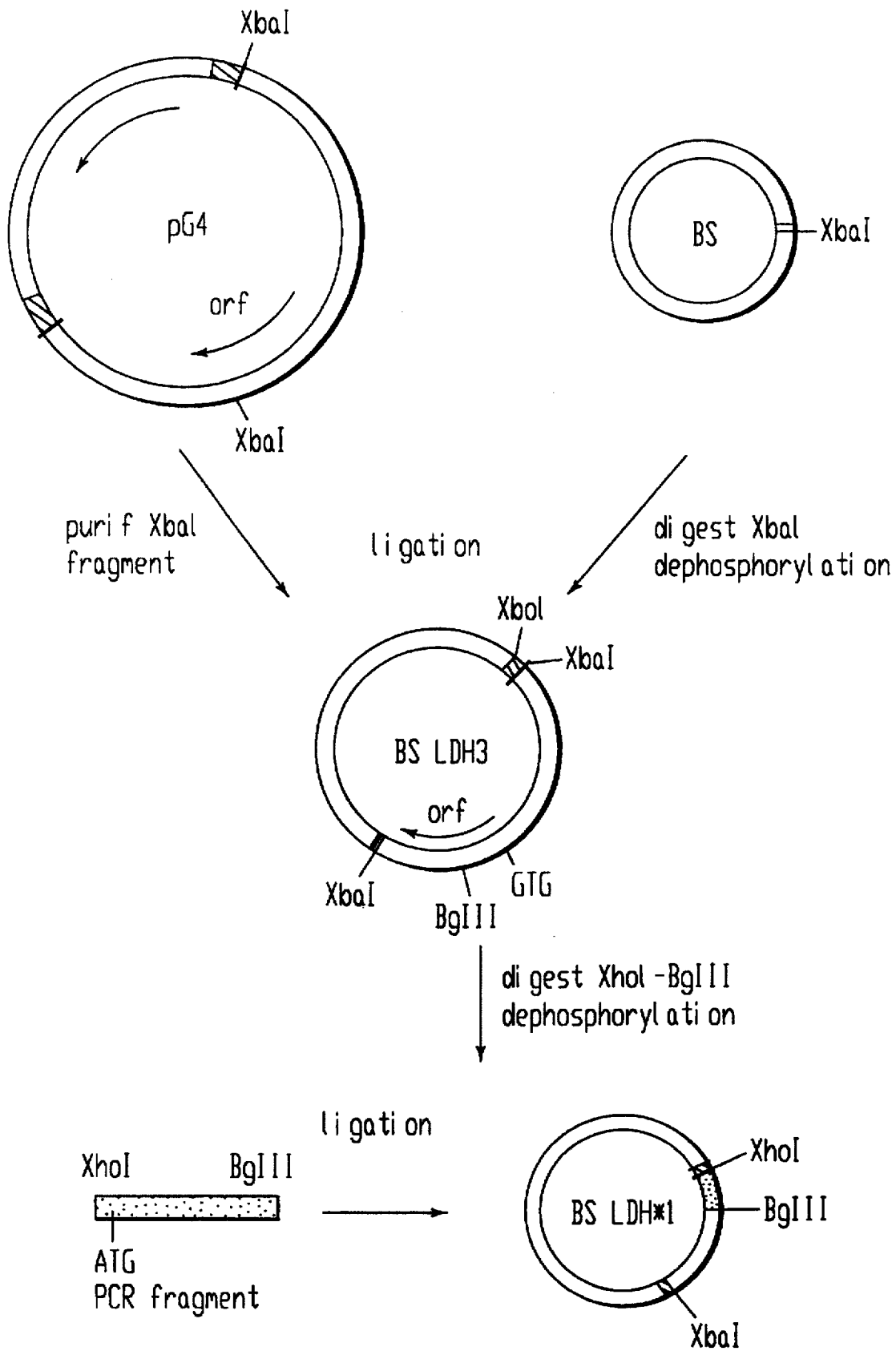
FIG. 2 diagrams the steps of reconstruction of the gene.

The different steps of this construction are shown diagrammatically in FIG. 2.

a) Construction of plasmid pBSLDH₃

The XbaI fragment (2.2 kb), bounded by a site downstream of the TAA stop codon and a site in the polylinker of plasmid pG4, was isolated by XbaI digestion of pG4, separation of the fragments on NIUSIEVE low-melting-temperature agarose gel (FMC) and cutting-out of the 2.2-kb band.

This fragment was subcloned into plasmid pBS (pBluescript II SK+, STRATAGENE) by ligation of 200 ng of XbaI fragment (in NIUSIEVE heated to 65° C.) to 50 ng of plasmid pBS digested with XbaI and dephosphorylated. The recombinant plasmid obtained is designated pBSLDH₃.

b) Introduction of the modified fragment

Plasmid pBSLDH₃ was digested with BglII (in the coding region) and XhoI (polylinker site) and then dephosphorylated.

100 ng of fragment amplified by PCR and digested with BglII/XhoI (as described in 1 above) were ligated to 50 ng of pBSLDH₃ thus treated.

Plasmid pBSLDH*₁ obtained possesses the coding region of the reconstituted LDH gene, with an ATG codon as initiation codon, bounded by an XhoI site immediately upstream of the ATG and by an XbaI site immediately downstream of the TAA stop codon.

The XhoI-BglII fragment of this plasmid was sequenced in order to verify, on the one hand the replacement of GTG with ATG, and on the other hand that no mistake was made by Taq polymerase during the amplification.

EXAMPLE 3

Introduction of the Modified Gene Into Expression Vectors

In order to obtain an expression of the mutagenized *L. casei* LDH gene in yeast, the coding region, comprising the ATG codon created, was placed under the control of yeast regulatory elements in a yeast/*E. coli* shuttle vector.

Figure 3:
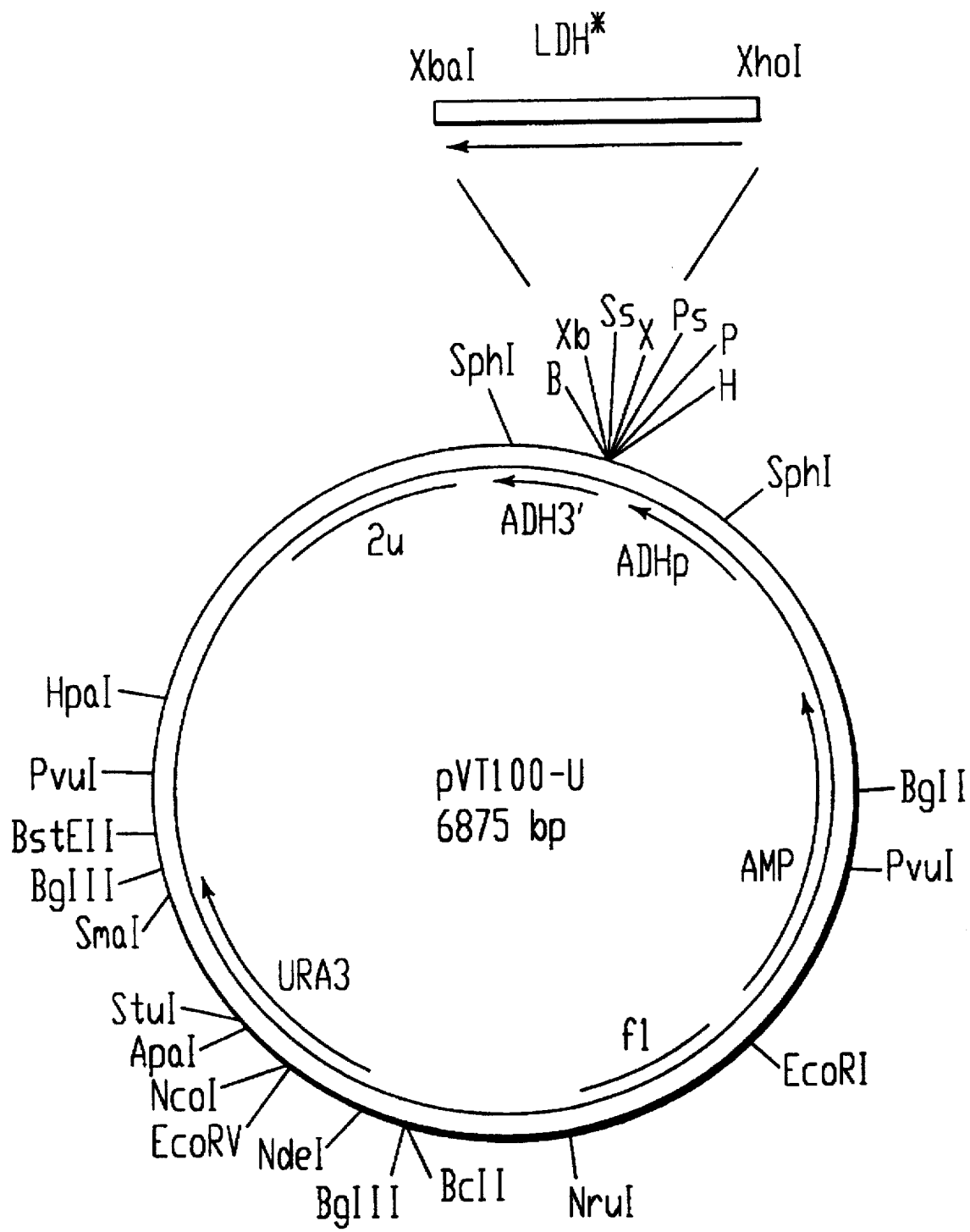
FIG. 3 shows the introduction of the LDH gene into the multicopy plasmid pVT100-U.

1) Introduction of the LDH gene into the multicopy plasmid pVT100-U (FIG. 3)

The expression plasmid which was used is plasmid pVT100-U containing the 2 B origin, the URA3 marker and the strong ADH regulatory elements (promoter and terminator), as well as the bacterial elements (origin and ampicillin-resistance gene).

This plasmid has been described by VERNET et al. [Gene 52:225–233, (1987)].

The XhoI-XbaI fragment of plasmid pBSLDH*₁ was isolated by XhoI/XbaI digestion and separation of the fragments on NIUSIEVE low-melting-temperature agarose gel. The XhoI-XbaI fragment (1 kb) corresponding to the gene was cut out.

100 ng of this fragment were ligated to 50 ng of vector pVT-100-U, the latter being digested with XbaI and XhoI (sites present in the polylinker) and dephosphorylated.

The recombinant vector pVT-100-ULDH* was obtained.

Figure 4:
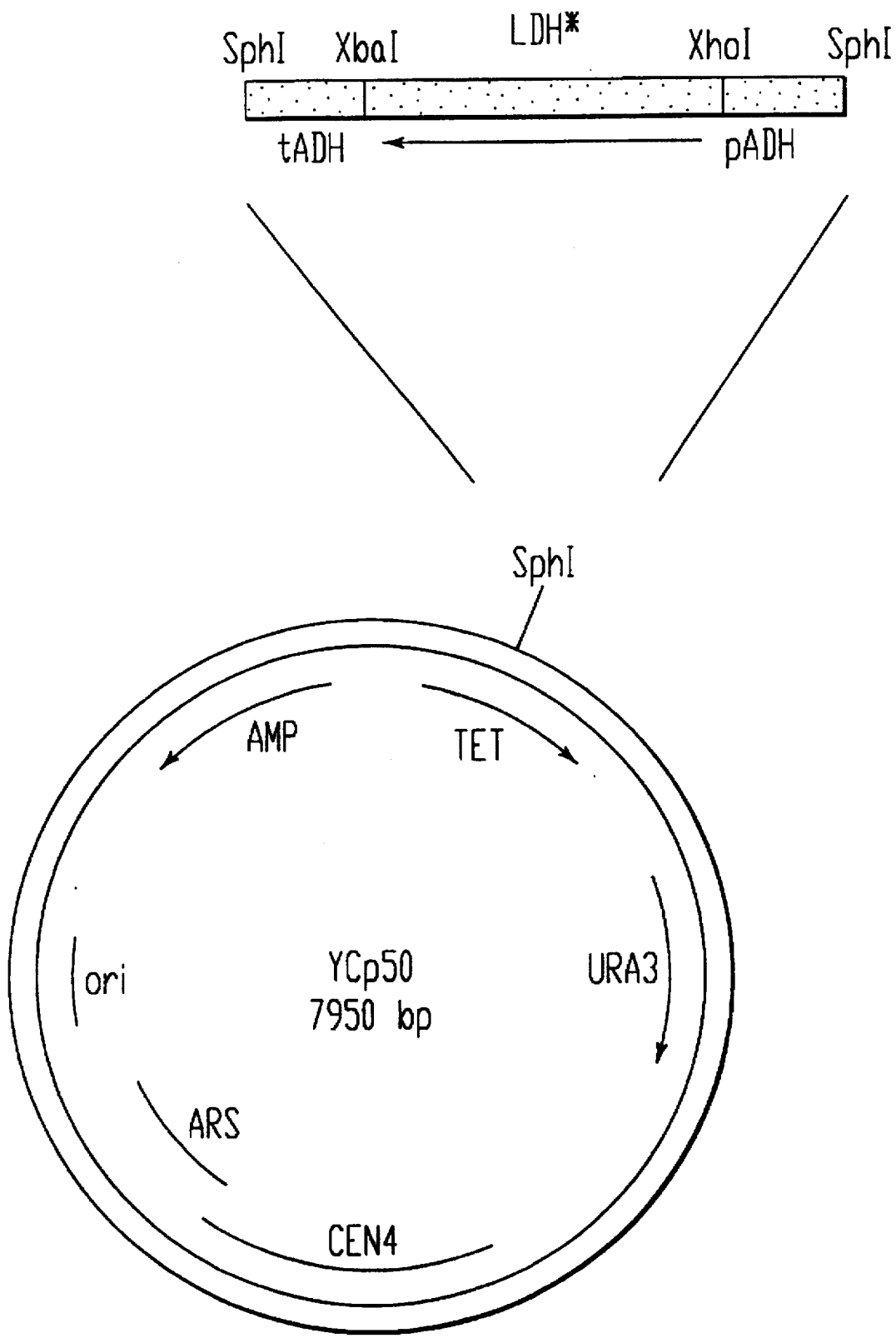
FIG. 4 shows the introduction of the LDH gene into the single-copy plasmid YCp50.

2) Introduction of the LDH gene into the single-copy plasmid YCp50 (FIG. 4)

The single-copy centromeric plasmid YCp50 has been described by ROSE [S. L. BERGER and A. R. KIMMEL (Ed), Academic Press, 481–504 (1987)].

This vector carries an ARS sequence and a centromeric sequence and the URA3 marker, as well as the bacterial elements (origin of replication and ampicillin resistance).

The SphI fragment of pVT 100-U-LDH* containing the pADH-LDH*-tADH expression cassette was isolated by SphI digestion and separation of the fragments on NIUSIEVE low-melting-temperature agarose gel. The SphI fragment containing the expression cassette (1.7 kb) was cut out. 100 ng of this fragment were ligated to 50 ng of vector YCp50, the latter being digested with SphI and dephosphorylated. The recombinant vector YCp50-LDH* was obtained.

EXAMPLE 4

Transformation of Yeast

*Saccharomyces cerevisiae* yeast strain SCV5M was transformed with plasmid pVT100-U-LDH* on the one hand and plasmid YCp50-LDH* on the other hand.

The strain SCV5M was deposited on Jun. 18 1992 with the Collection Nationale de Cultures de Microorganismes [National Collection of Microorganism Cultures] held by the Pasteur Institute, under number I-1222. The organism is a haploid laboratory strain, auxotrophic for uracil (ura3), MAT a, derived from an enological strain. This strain is capable of developing a fermentation under enological conditions comparable to those of industrial strains.

The transformation method used is the lithium acetate method described by GIETZ and SCHIESTL [Yeast, 7:253–263, (1991)].

The selective medium used is YNB (Yeast nitrogen base 7 g/l DIFCO, glucose 20 g/l). The absence of uracil enables a selection pressure to be preserved for the plasmid.

EXAMPLE 5

Fermentation Tests

1) Multicopy plasmid pVT100-U-LDH*

Fermentation tests were carried out with the following strains:

V5/pVT100-U: strain SCV5M transformed with plasmid pVT100-U without insert, as a control.

V5/pVT100-U-LDH*: strain SCV5M transformed with the multicopy plasmid pVT100-U containing the modified LDH gene. Several transformants were tested separately.

Fermentations were carried out on YNB (yeast nitrogen base 7 g/l, DIFCO) minimum synthetic medium containing 50 g/l of glucose and buffered to pH 5.1 with 6.3 g/l of citric acid and NaOH.

Preculturing of the strains V5/pVT100-U and V5/pVT100-U-LDH* was carried out for 20 hours in 10 ml of medium at 28° C.

Culturing was carried out in 50 ml, by inoculation of 7×10⁵ cells/ml from the precultures. The number of cells was determined on a COULTER COUNTER model ZBI type apparatus.

The cultures were incubated at 28° C. with intermittent stirring with a bar magnet.

The initial pH was measured: 5 for V5/pVT100-U and 4.9 for V5/pVT100-U-LDH*.

1-ml samples were withdrawn at regular intervals to determine:

the number of cells, by cell counting (COULTER COUNTER);

the pH of the culture medium;

the glucose, ethanol and lactate concentration of the culture medium, by enzymatic assay (BOEHRINGER assay kits);

the lactate dehydrogenase specific activity; this activity was determined on crude cell extracts obtained as follows: $10^8$ cells are withdrawn, centrifuged for 5 minutes at 6000 rpm and washed in 5 ml of 80 mM acetate buffer, pH 5.5 (0.2M acetate buffer: 2.73 g Na acetate in 100 ml of water; pH 5.5 with acetic acid). The cell pellet is taken up in 0.5 ml of the same buffer. The cells are ground on a vortex mixer using glass beads, for 4 times 1 minute, in the cold state. The ground preparation is centrifuged for 5 minutes at 15000 rpm, and the supernatent recovered is used as crude extract. The LDH assay is carried out as described by HENSEL et al. [Arch. Microbiol. 112, 81–93 (1977)]. The LDH activity is expressed in U/mg of proteins of the extract.

The results of the assays performed are as follows:

Ethanol and lactate production:

The lactate production of V5/pVT100-U-LDH* varies, depending on the transformants tested, betweeen 6 and 25 g/l of lactate, with an amount produced of the order of 10 g/l in most cases; the experimental results detailed below and illustrated in FIG. 5 were obtained with a transformant V5/pVT100-U-LDH* producing approximately 10 g/l of lactate. Whereas the control strain produces ethanol but does not show detectable lactate production (FIG. 5D), the transformant simultaneously produces lactate and ethanol (FIG. 5C), which corresponds approximately to the degradation of 25 to 30% of the glucose present in the culture medium to lactate.

The simultaneous production of lactate and ethanol is, furthermore, demonstrated throughout the exponential growth phase and at the beginning of the stationary phase. During the stationary phase, lactate production stops.

Figure 5A:
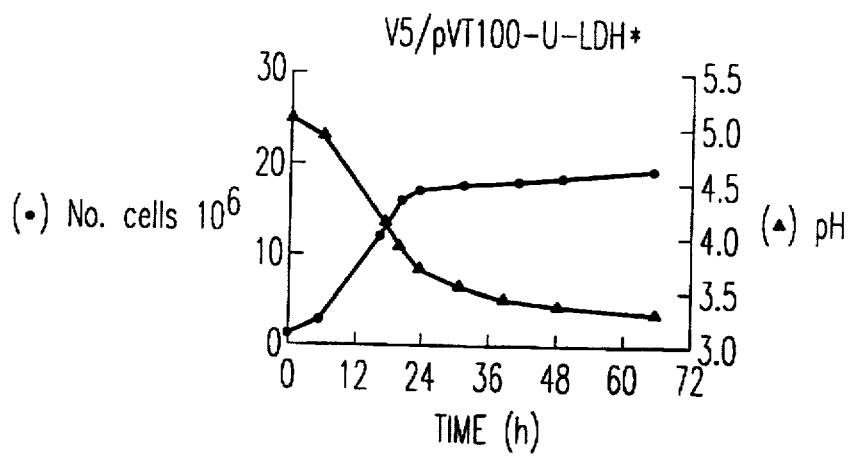
FIGS. 5A and 5B show the growth of transformant V5/pVT100-U-LDH* and a control strain, respectively.
Figure 5B:
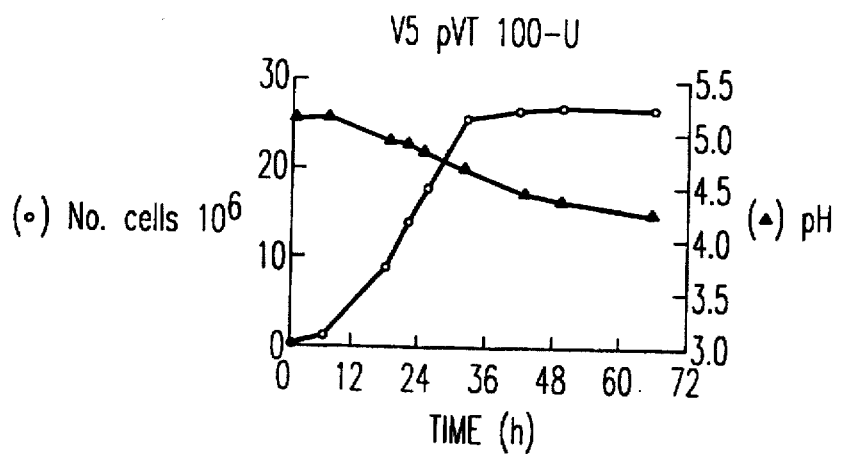
Figure 5C:
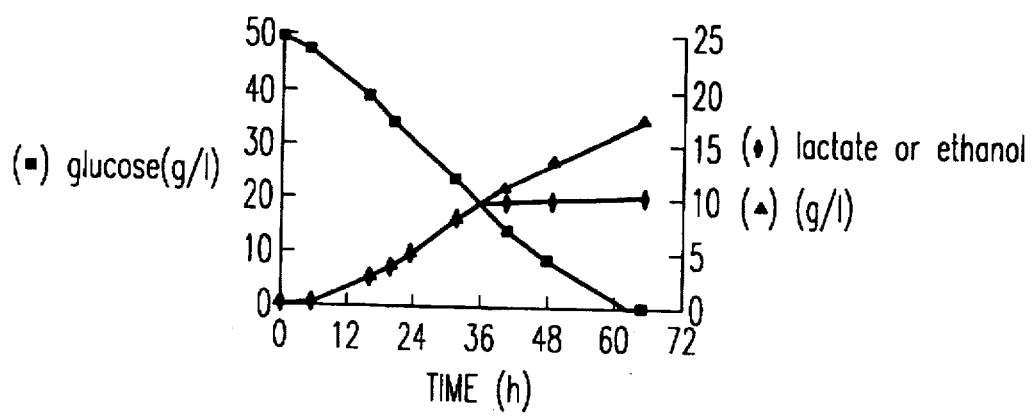
FIGS. 5C and 5D show the lactate and ethanol production of transformant V5/pVT100-U-LDH* and a control strain, respectively.
Figure 5D:
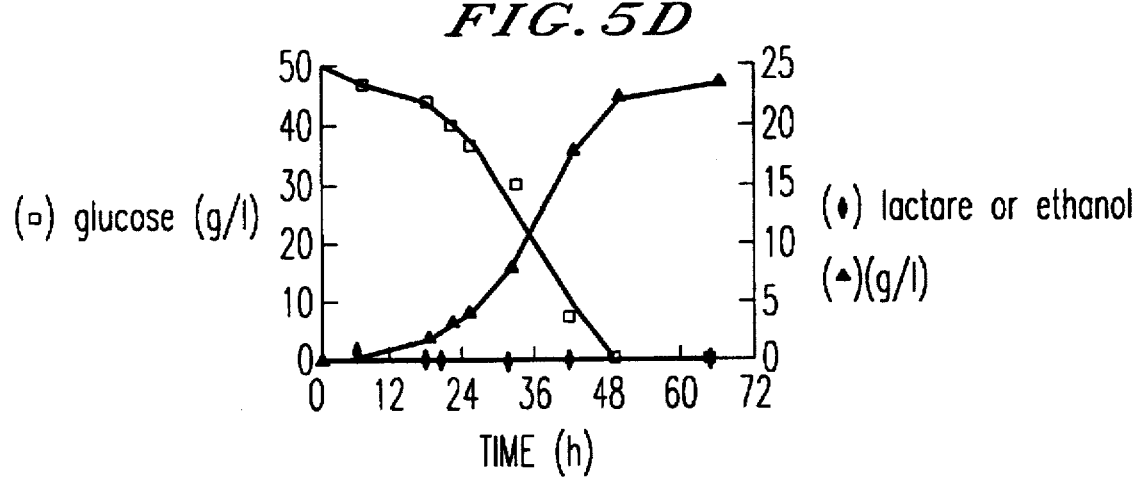
Figure 5E:
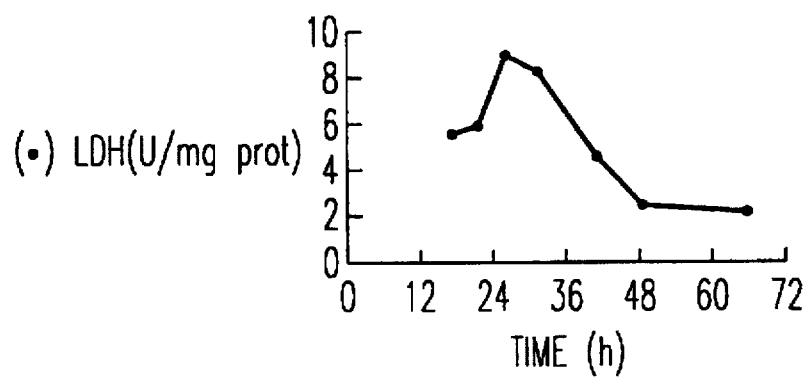
FIG. 5E shows the specific activity of LDH over time for the transformant V5/pVT100-U-LDH*.

Cell growth:

The growth of the transformant V5/pVT100-U-LDH* (FIG. 5A) is comparable to that of the control strain (FIG. 5B). The cessation of growth (onset of the stationary phase) takes place, however, earlier for the transformed strain than for the control, and the final number of cells is approximately 20 % lower than that observed for the control strain.

Measurement of the pH of the culture medium

The cessation of growth may be explained by the substantial acidification of the culture medium. A much greater fall in pH is, in effect, observed in the case of the transformed strain (FIG. 5A) than in the case of the control strain (FIG. 5B). This substantial acidification correlates fully with the observed lactate production.

Assay of LDH activity:

The results obtained on the crude extract of the transformed strain (FIG. 5E) show that the LDH specific activity is maximal when the cells enter the stationary phase, and then decreases during this same phase.

Other culture media:

The results obtained on YNB medium were, in addition, confirmed on grape juice (185 g/l glucose) and apple juice (93 g/l glucose).

The obtaining of a lactate/ethanol mixed production may hence be achieved on different media (synthetic, minimum or complete, natural) containing variable glucose concentrations, and irrespective of the starting pH. The temperature range which can be used is that permitting the growth of yeasts (approximately 14°–35° C.).

2) Single-copy plasmid YCp50-LDH*

Fermentation tests were carried out with the strain V5/YCp50-LDH* on YNB medium containing 50 g/l of glucose buffered to pH 5.1. A lactate production of the order of 1 g/l was obtained for this strain.

The LDH specific activity, determined as described above, displays variations similar to those observed with the multicopy transformants. In contrast, the maximal activity observed at the end of the exponential phase/beginning of the stationary phase is of the order of 1.5 U/mg proteins, equivalent to one seventh of the maximal activity obtained with the multicopy transformant (10 U/mg prot.).

Lactate production by the single-copy transformant hence correlates with the level of LDH specific activity.

This shows that the production of lactate may be modulated, in particular, in accordance with the number of LDH genes introduced into the yeast.

As is apparent from the foregoing, the invention is in no way limited to those of its embodiments and modes of implementation and application which have just been described more explicitly; it encompasses, on the contrary, all variants which may occur to the specialist in the field, without departing from the context or the scope of the present invention.

We claim:

1. A recombinant yeast strain for use in alcoholic fermentation and which comprises at least one copy of a gene coding for a lactic dehydrogenase (LDH) derived from a lactic acid bacterium, under the control of sequences regulating the expression of said gene in yeast.

2. The recombinant yeast strain of claim 1, wherein said yeast is of the genus Saccharomyces.

3. The recombinant yeast strain of claim 1, wherein said lactic acid bacterium is *Lactobacillus casei*.

4. A yeast expression cassette which comprises a gene coding for a lactic dehydrogenase (LDH) derived from a lactic acid bacterium operatively linked to at least one regulatory sequence which is active in yeast.

5. An expression vector which comprises an expression cassette which comprises a gene coding for a lactic dehydrogenase (LDH) derived from a lactic acid bacterium operatively linked to at least one regulatory sequence which is active in yeast.

6. The expression vector of claim 5, which is a shuttle vector and which further comprises a bacterial origin of replication and a marker which is selectable in a bacterium.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i x ) FEATURE:
        ( A ) NAME/KEY: Peptide
        ( B ) LOCATION: 1..6
        ( D ) OTHER INFORMATION: /note= "amino acids 5-10 of L-LDH
        published by Hensel et al, Eur. J. Biochem. 134:503
        ( 1 9 8 3 )"

( x i ) SEQUENCE DESCRIPTION: SEQ ID NO:1:

Asp Lys Asp His Gln Lys
1             5

( 2 ) INFORMATION FOR SEQ ID NO:2:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Peptide
      ( B ) LOCATION: 1..6
      ( D ) OTHER INFORMATION: /note= "amino acids 262-267 of L-LDH
         published by Hensel et al, Eur. J.Biochem. 134:503-511
         ( 1 9 8 3 )."

( x i ) SEQUENCE DESCRIPTION: SEQ ID NO:2:

Tyr Met Asp Gly Gln Tyr
1             5

( 2 ) INFORMATION FOR SEQ ID NO:3:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:3:

GAYAARGAYC AYCARAA         17

( 2 ) INFORMATION FOR SEQ ID NO:4:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:4:

TAYTGNCCRT CCATRTA         17

( 2 ) INFORMATION FOR SEQ ID NO:5:

( i ) SEQUENCE CHARACTERISTICS:
      ( A ) LENGTH: 22 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:5:

GGCTCGAGAT GGCAAGTATT AC         22

( 2 ) INFORMATION FOR SEQ ID NO:6:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( x i ) SEQUENCE DESCRIPTION: SEQ ID NO:6:

GATATCACCG TGGCAAGTAT TAC         23

( 2 ) INFORMATION FOR SEQ ID NO:7:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:7:

TGAAGATCTT GAAGTCCATT GT 22

( 2 ) INFORMATION FOR SEQ ID NO:8:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:8:

ACAATGGACT TCAAGATCTT CA 22